(12) United States Patent
Singleton

(10) Patent No.: US 8,697,035 B2
(45) Date of Patent: Apr. 15, 2014

(54) SKIN CARE COMPOSITIONS

(75) Inventor: Laura C. Singleton, Los Angeles, CA (US)

(73) Assignee: Neutrogena Corporation, Los Angeles, CA (US)

(*) Notice: Subject to any disclaimer, the term of this patent is extended or adjusted under 35 U.S.C. 154(b) by 0 days.

(21) Appl. No.: 13/170,583

(22) Filed: Jun. 28, 2011

(65) Prior Publication Data

US 2012/0014882 A1    Jan. 19, 2012

Related U.S. Application Data

(60) Provisional application No. 61/460,756, filed on Jul. 14, 2010.

(51) Int. Cl.
*A61K 8/34* (2006.01)
*A61K 8/37* (2006.01)
*A61K 8/891* (2006.01)
*A61K 8/895* (2006.01)
*A61Q 17/04* (2006.01)

(52) U.S. Cl.
USPC ............................................ 424/45; 424/400

(58) Field of Classification Search
CPC ....... A61K 2800/31; A61K 8/34; A61K 8/37; A61K 8/891; A61K 8/895; A61Q 17/04
USPC ......................................................... 424/45
See application file for complete search history.

(56) References Cited

U.S. PATENT DOCUMENTS

| | | | |
|---|---|---|---|
| 4,551,330 A | 11/1985 | Wagman et al. | |
| 4,671,955 A | 6/1987 | Palinczar | |
| 4,686,099 A * | 8/1987 | Palinczar | 424/47 |
| 4,710,371 A | 12/1987 | Palinczar | |
| 5,118,507 A | 6/1992 | Clement | |
| 5,152,983 A | 10/1992 | Nambudiry et al. | |
| 5,216,033 A | 6/1993 | Pereira et al. | |
| 5,962,018 A | 10/1999 | Curtis et al. | |
| 6,197,281 B1 | 3/2001 | Stewart et al. | |
| 2001/0053348 A1 | 12/2001 | Stewart et al. | |
| 2004/0067206 A1 | 4/2004 | Paspaleeva-Kuhn et al. | |
| 2004/0136932 A1 | 7/2004 | Rozot et al. | |
| 2005/0013782 A1* | 1/2005 | Goppel et al. | 424/59 |
| 2006/0128883 A1 | 6/2006 | Garrison et al. | |
| 2007/0116696 A1 | 5/2007 | Riley | |
| 2008/0014155 A1 | 1/2008 | Marrs | |
| 2009/0035234 A1 | 2/2009 | Cunningham et al. | |
| 2010/0092410 A1 | 4/2010 | Cockerell et al. | |
| 2010/0135939 A1 | 6/2010 | Lehmann et al. | |
| 2010/0310481 A1 | 12/2010 | Chevalier et al. | |
| 2011/0200543 A1 | 8/2011 | Josso | |

FOREIGN PATENT DOCUMENTS

| | | |
|---|---|---|
| WO | WO 2005/004820 A | 1/2005 |
| WO | WO 2011/097448 A | 8/2011 |

OTHER PUBLICATIONS

CosmoSurf technical data sheet, Dec. 2009.*
Silwax technical data sheet Nov. 2009.*
Natural Sourcing, Lotus Flower Wax technical data sheet, Oct. 16, 2008.*
Natural Sourcing, description page 2007-2012.*
Chen et al., "Evaluation of Antioxidant and DNA Protection Activities in the Extracts of Leaves of the Lotus Plant", *Chia Nan University of Pharmacy & Science Institutional Repository* (Aug. 2009).
CosmoSurf CE-100 Data Sheet, http://www.surfatech.com/pdfs/MSDS%20Cosmosurf%20CE-100.pdf Retrieved Dec. 18, 2011 Section 1.
Kim et al., "Prediction of Interfacial Tension between Oil Mixtures and Water", Journal of Colloid and Interface Science, 241(2):509-513 (Sep. 15, 2001).
Hughes et al., "Novel Methods for Emollient Characterization", Cosmetics and Toiletries Manufacture Worldwide, pp. 19-24 (2006).
"Densities of Homosalate, Octisalate, Octocylene, and Butyloctyl Salicylate", Registry database (STN), pp. 1-13, Search done Jan. 19, 2013.
Evonik Industries, "Tegosoft® PBE", Evonik Goldschemidt GmbH, <www.evonik.com/personal-care>, published Feb. 2008, pp. 1-3.
EWG's Skin Deep® Cosmetics Database, "PPG-14 Butyl Ether", <http://www.ewg.org/skindeep/ingredient/705247/PPG-14_BUTYL_ETHER/>, © 2007-2013, pp. 1-3.

* cited by examiner

*Primary Examiner* — Abigail Fisher
*Assistant Examiner* — Luke Karpinski

(57) ABSTRACT

Anhydrous sunscreen compositions that include a volatile solvent, an organic UV-filter dissolved in the volatile solvent, a water-insoluble, low-volatility, $C_2$-$C_8$, liquid silicone dissolved in the volatile solvent, a branched fatty acid ester of a polyprotic carboxylic acid dissolved in the volatile solvent, and a film-forming polymer, where the branched fatty acid ester of a polyprotic carboxylic acid and the water-insoluble, low-volatility, $C_2$-$C_8$, liquid silicone are present in a ratio from about 3:1 to 4.25:1.

17 Claims, No Drawings

SKIN CARE COMPOSITIONS

This application claims the benefit of U.S. provisional application 61/460,756 filed on Jul. 14, 2010, the complete disclosure of which is hereby incorporated by reference.

FIELD OF THE INVENTION

The present invention relates to topical sunscreen compositions having the ability to be successfully applied to wet skin.

BACKGROUND OF THE INVENTION

Conventional sunscreen products generally take the form of UV-filter compounds and/or particulate UV-screening compounds (collectively, "sunscreen actives") that are solubilized, emulsified, or dispersed in a vehicle, which is topically applied to the skin. The sunscreen actives, typically through the aid polymers and other ingredients included in the vehicle, form a thin, protective, and often water-resistant layer on the skin.

The applicants have recognized that, unfortunately, while typical sunscreen products are successful at providing a durable protective barrier when applied to dry skin, such is not typically the result when applied to skin that is damp with sweat or has residual water thereon. In fact, when applied to wet skin, the tendency of conventional sunscreen products is to dilute the sunscreen actives, smear, and form an incomplete film, often one that flakes or peels off the skin, and/or takes on a pasty, white appearance. The end result is unattractive, and renders the skin with poor protection from the sun's rays.

Others have contemplated a solution to this problem by using a water-in-oil emulsifier to "self-emulsify," presumably in the presence of residual water present on the skin. However, the applicants have recognized that severe aesthetic and performance problems still exist in prior art "wet skin" sunscreen products. Accordingly, the applicants have now identified an entirely new composition that provides consistent and pleasant application to the skin as well as the ability of the resulting film to protect the skin from damaging ultraviolet radiation.

SUMMARY OF THE INVENTION

The present invention relates to anhydrous sunscreen compositions comprising a volatile solvent, an organic UV-filter dissolved in the volatile solvent; a water-insoluble, low-volatility, $C_2$-$C_8$, liquid silicone dissolved in the volatile solvent, a branched fatty acid ester of a polyprotic carboxylic acid dissolved in the volatile solvent, and a film-forming polymer. The branched fatty acid ester of a polyprotic carboxylic acid and the water-insoluble, low-volatility, $C_2$-$C_8$, liquid silicone is present in a ratio from about 3:1 to 4.25:1.

DETAILED DESCRIPTION OF THE INVENTION

The present invention meets the aforementioned need and overcomes the disadvantages of the prior art. In particular, it has been discovered that organic ultraviolet (UV) filters can be combined with a volatile solvent, a water-insoluble, low-volatility, $C_2$-$C_8$, liquid silicone, a branched fatty acid ester of a polyprotic carboxylic acid, and a film-forming polymer to form an anhydrous composition that surprisingly forms a durable, aesthetic, protective film when applied to wet skin.

As used herein, "cosmetically acceptable" means suitable for use in contact with tissues (e.g., the skin) without undue toxicity, incompatibility, instability, irritation, allergic response, or the like.

As used herein, "substantially free" means the composition contains less than about 1, such as less than about 0.1, e.g., less than about 0.01 weight percent of an ingredient.

Compositions of the present invention are anhydrous. By "anhydrous" it is meant that the composition is substantially free of water.

As used herein, "whitening" refers to a non-transparent or milky appearance attributable to contact of the sunscreen compositions with water on the skin.

Concentration Ranges and "Concentrate"

Unless otherwise specifically described, all percentages included herein are percentages by weight, based on total weight of the composition, excluding any propellant that is present. The composition excluding any propellant is referred to in this specification as a "concentrate."

Organic-UV Filter

Compositions of the present invention include an organic UV-filter. Organic UV filters that are useful in the present invention are cosmetically-acceptable compounds that absorb radiation in the UV range and are generally soluble in one or more organic hydrocarbon solvents. The organic, UV-filter absorbs radiation in some portion of the ultraviolet spectrum (290 nm-400 nm), and may have an extinction coefficient of at least about 1000 $mol^{-1}$ $cm^{-1}$, for example greater than 10,000 or 100,000 or 1,000,000 $mol^{-1}$ $cm^{-1}$, for at least one wavelength within the above-defined ultraviolet spectrum.

Examples of organic UV filters include, without limitation, 3-benzylidene camphor, specifically 3-benzylidene norcamphor and derivatives thereof, e.g. 3-(4-methylbenzylidene) camphor; 4-aminobenzoic acid derivatives, specifically 4-(dimethylamino)benzoic acid-2-ethylhexyl esters, 4-(dimethylamino)benzoic acid-2-octyl esters and 4-(dimethylamino)benzoic acid amylesters; esters of cinnamonic acid, in particular 4-methoxycinnamonic acid-2-ethylhexylester, 4-methoxycinnamonicacid propylester, 4-methoxycinnamic acid isoamyl ester, 2-cyano-3,3-phenylcinnamonic acid-2-ethylhexyl ester (octocrylene); esters of salicylic acid, i.e., salicylic acid-2-ethylhexylester, salicylic acid-4-isopropylbenzyl ester, salicylic acid homomenthyl ester; derivatives of benzophenones, in particular 2-hydroxy-4-methoxybenzophenone, 2-hydroxy-4-methoxy-4'-methylbenzophenone, 2,2'-dihydroxy-4-methoxybenzophenone; esters of benzalmalonic acid, in particular 4-methoxybenzmalonic acid di-2-ethylhexyl ester; triazine derivatives, for example 2,4,6-trianilino-(p-carbo-2'-ethyl-1'-hexyloxy)-1,3,5-triazine and octyltriazone; or benzoic acid, 4,4'-[[6-[[[(1,1-dimethylethyl)amino]carbonyl]phenyl]amino]-1,3,5-triazine-2,4-diyl]diimino]bis-, bis (2-ethylhexyl) ester (UVASORB HEB); propane-1,3-diones, for example, 1-(4-tert.butylphenyl)-3-(4'-methoxyphenyl) propane-1,3-dione; ketotricyclo (5.2.1.0) decane derivatives; derivatives of benzoylmethane, for example, 1-(4'-tert.butylphenyl)-3-(4'-methoxyphenyl) propane-1,3-dione, 4-tert-butyl-4'-methoxydibenzoylmethane (PARSOL 1789), 1-phenyl-3-(4'-isopropylphenyl)-propane-1,3-dione, derivatives of benzoic acid 2-(4-diethylamino-2-hydroxybenzoyl)-benzoic acid hexylester (UVINUL A+), or 1H-benzimidazole-4,6-disulfonic acid, 2,2'-(1,4-phenylene)bis-, disodium salt (NEO HELOPAN AP); and benzotriazoles, in particular the benzotriazole derivative known as 2,2'-methylene-bis-(6-(2H-benzotriazole-2-yl)-4-(1,1,3,3-tetramethylbutyl)-phenol) [INCI: Bisoctyltriazol], which is commercially available under the tradename TINOSORB M from CIBA Chemicals. Another useful benzotriazole derivative is 2-(2H-benzotriazole-2-yl)-4-methyl-6-[2-methyl-3-[1,3,3,3-tetramethyl-1-[(trimethylsilyl)oxy]disiloxanyl]propyl]-phenol (CAS-No.: 155633-54-8), also identified by the INCI name drometrizole trisiloxane and available from Chimex under the tradename MEXORYL XL. Also suitable are asymmetrically substituted triazine derivatives, and 2,4-bis-{[4-(2-ethyl-hexyloxy)-2-hydroxy]-phenyl}-6-(4-methoxyphenyl)-1,3,5-triazine (INCI: anisotriazine) that is commercially available under the tradename TINOSORB S from CIBA.

In one embodiment, the organic UV-filter is selected from the group consisting of octocrylene, a benzotriazole, anisotriazine, an ester of salicylic acid, an ester of cinnamic acid and a derivative of a benzoylmethane.

The organic, UV-filter may be present in the concentrate in a range from about 1% to about 40%, such as from about 5% to about 35%, such as from about 10 to about 30%, e.g., from about 15 to about 25% by weight.

As one skilled in the art will readily appreciate the term "organic UV filter" does not include ultraviolet-screening particles ("UV-screening particles") typically used at least in part to scatter ultraviolet radiation. Examples include inorganic oxides, including titanium dioxide, zinc oxide, iron oxides, silicone oxides, or other metal (e.g., transition metal, such as crystalline transition metal) oxides. UV-screening particles are typically solid particles having a dimension (e.g., a diameter) from about 0.1 micron to about 10 microns. In certain embodiments of the invention, UV-screening particles may optionally be included in compositions. In certain other embodiments they are excluded. For those embodiments in which UV-screening particles are included, the concentration of the UV-screening particles in the concentrate may be from about 0.1% to about 10%, such as from about 0.5% to about 5%, such as from about 0.5% to about 2%.

Volatile Solvent

Compositions of the present invention include a volatile solvent. By "volatile" it is meant compounds that meet one or more of the following requirements: those compounds with a flash point below 150° C., such as less than about 130° C., such as less than about 50° C., such as less than about 25° C., and/or a boiling point of less than about 150° C., such as less than about 100° C., such as less than about 90° C. By solvent it is meant, a compound that is capable (absent any other ingredients such as surfactants, co-solvents, etc.) of dissolving (e.g., forming a clear solution, such as one that transmits at least 25%, such as at least about 50% of light intensity of a 700 nm wavelength source through a 1 cm path length, as measured by conventional visible spectrophotometry) the UV-filter present in the composition when the concentration of UV-filter in the volatile solvent is set at 1% of the volatile solvent. In certain embodiments, the solution can be obtained when the concentration of UV-filter in the volatile solvent is set at 10%.

The volatile solvent is generally cosmetically-acceptable and is a liquid at room temperature. Furthermore, the volatile solvent is, in certain embodiments, miscible with water. By "miscible with water" it is meant that the volatile solvent is fully soluble in water in all proportions. Suitable examples of volatile solvents that are miscible with water include ethanol, propanol, and isopropanol. The volatile solvent, if not miscible with water, may, in certain embodiments, be soluble to at least some extent in isopropanol.

The amount of volatile solvent present in the concentrate may be from about 10% to about 60%, or from about 20% to about 55%, or from about 30% to about 50%.

Water-Insoluble, Low-Volatility $C_2$-$C_8$ Liquid Silicone

Compositions of the present invention include a water-insoluble, low-volatility, $C_2$-$C_8$, liquid silicone. By "low-volatility" it is meant compounds that have a flash point above about 105° C., such as above about 150° C., such as above about 200° C. By liquid silicone, it is meant, a compound having at least one siloxane (Si—O—Si linkage) and which is liquid at room temperature (melting point is below 25° C.). The liquid silicone is insoluble in water, but generally soluble in the volatile solvent (e.g., soluble in isopropanol). The liquid silicone includes a $C_2$-$C_8$ functional group. In certain embodiments it may have siloxy repeat units with pendant alkyl groups, such as those that include one or multiple units of:

—[CH$_3$—SiO—C$_n$H$_{2n}$—CH$_3$]— where n is from 2-8, such as from 2-4. A particularly suitable example is the compound in which n=2, available as SILWAX D02 (INCI: ethyl methicone) from Siltech of Dacula, Ga. In another embodiment, the liquid silicone is caprylyl methicone. In yet another embodiment, the liquid silicone is phenyl trimethicone.

The water-insoluble, low-volatility, $C_2$-$C_8$, liquid silicone generally functions to provide plasticity to the film that is created on the skin, and to prevent whitening (e.g., by increasing the refractive index of the resulting film) that might otherwise occur when the composition contacts water present on the skin.

The amount of water-insoluble, low-volatility, $C_2$-$C_8$, liquid silicone present in the concentrate may be from about 0.5% to about 10%, or from about 1% to about 6%, or from about 2% to about 4%.

Branched Fatty Acid Ester of a Polyprotic Carboxylic Acid

Compositions of the present invention include a branched fatty acid ester of a polyprotic carboxylic acid ("BFEPCA"). The branched fatty acid ester of a polyprotic carboxylic acid is a liquid at room temperature (melting point is below 25° C.), is water-insoluble and is soluble in the volatile solvent. In a notable embodiment, the BFEPCA is a reaction product of a polyprotic acid with a $C_{10}$-$C_{30}$ fatty acid, such as a $C_{12}$-$C_{22}$ fatty acid. The fatty acid may be branched. The polyprotic acid may be selected from the group consisting of citric acid, ascorbic acid, phosphoric acid and sulfuric acid. In one embodiment, the polyprotic acid is citric acid or ascorbic acid. Citric acid is particularly notable.

For example, the BFEPCA may have five or more ester groups per molecule. One suitable example of a BFEPCA is an octyldodecyl citrate polyester which is commercially available as COSMOSURF CE-100 from SurfaTechCorporation/Siltech Corporation of Dacula, Ga.

The PFECPA assists the ability of the composition to exclude water during formation of the film, yet also serves to prevent peeling in the film and resist degradation from water after the film forms.

The amount of PFECPA present in the concentrate may be from about 2% to about 40%, or from about 4% to about 25%, or from about 8% to about 18%. The inventors have found that PFEPCA and the water-insoluble, low-volatility, $C_2$-$C_8$, liquid silicone should be present in a PFEPCA to water-insoluble, low-volatility, $C_2$-$C_8$, liquid silicone ratio that is from about 3:1 to 4.25:1, such as from 3.5:1 to 4:1. If the ratio is too high, the composition exhibits undesirable temporary whitening when applied to wet skin and the film does not form properly, does not have good aesthetics, e.g. it has a heavy feel on skin, and tends to peel on contact with wet skin, whereas if the ratio is too low, the resulting film lacks water-resistance.

Film-Forming Polymer

Compositions of the present invention include a film forming polymer to enhance film formation and provide some water resistance. By "film-forming polymer," it is meant a polymer that when dissolved in the composition, permits a continuous or semi-continuous film to be formed when it the composition is spread onto, e.g., smooth glass, and the liquid vehicle is allowed to evaporate. As such, the polymer should dry on the glass in a manner in which over the area which it is spread should be predominantly continuous, rather than forming a plurality of discrete, island-like structures. Generally, the films formed by applying compositions on the skin according to embodiments of the invention described herein, are less than, on average, about 100 microns in thickness, such as less than about 50 microns.

Suitable film-forming polymers include natural polymers such as polysaccharides or proteins and synthetic polymers such as polyesters, polyacrylics, polyurethanes, vinyl polymers, polysulfonates, polyureas, polyoxazolines, and the like. Specific examples of film-forming polymers include, for example, acrylic homopolymers or copolymers with hydrophobic groups such as acrylate/ocylacrylamide copolymers including DERMACRYL 79 available from Akzo Chemical of Bridgewater, N.J.; dimethicone/acrylates dimethicone copolymer available as X-22-8247D from Shin-Etsu of Japan; hydrogenated dimer dilinoleyl/dimethylcarbonate copolymer, available from Cognis Corporation of Ambler, Pa. as COSMEDIA DC; copolymer of vinylpyrrolidone and a long-chain a-olefin, such as those commercially available from ISP Specialty Chemicals of Wayne, N.J. as GANEX V220; vinylpyrrolidone/tricontanyl copolymers available as GANEX WP660 also from ISP; water-dispersible polyesters, including sulfopolyesters such those commercially available from Eastman Chemical as EASTMAN AQ 38S. In certain embodiments, the film-forming polymer is water insoluble, but is rendered soluble upon exposure to alkalinity in order to facilitate removal from the skin upon washing with soap.

The amount of film-forming polymer present in the concentrate may be from about 0.25% to about 15%, or from about 0.5% to about 10%, or from about 1% to about 5%.

Dispersed Alkyl-Modified Silicone Polymer

Compositions of the present invention may include a dispersed alkyl-modified silicone polymer. The dispersed alkyl-modified silicone polymer is generally insoluble in the volatile solvent as well insoluble in water. In order to confer insolubility in both water and in the volatile solvent, the dispersed alkyl-modified silicone polymer includes a $C_8$-$C_{30}$ linear or cyclic, saturated or unsaturated alkyl group such as a $C_{12}$-$C_{22}$ alkyl group.

The dispersed alkyl-modified silicone generally serves to reduce surface tension, improve water exclusion and reduce whitening. An example of a suitable alkyl-modified silicone polymer that disperses well in volatile solvents such as isopropanol include copolymers of cetyl dimethicone and bis-vinyl dimethicone, such as SILWAX CR-5016, commercially available from SilTech of Dacula, Ga.

The amount of dispersed alkyl-modified silicone polymer present in the concentrate may be from about 0.1% to about 1%, or from about 0.1% to about 0.5%, or from about 0.1% to about 0.25%.

Aerosol Propellant

Compositions of the present invention may include a propellant to aid in spraying the composition onto the skin. The inventors have found that whitening can be reduced by having the composition substantially free of water insoluble propellants such as isobutane. If a propellant is chosen, a propellant that has finite (non-zero) solubility in water may be used. One suitable example is an ether such as dimethyl ether (which has a water solubility of 71 g/liter at 20° C.) and methyl ethyl ether, with dimethyl ether being particularly notable.

The amount of aerosol propellant may be present in the composition from about 10% to about 60%, or from about 20% to about 40%, or from about 25% to about 40%. As discussed previously, the remainder of the composition is the concentrate.

In an alternative embodiment, rather than include a conventional aerosol propellant, the composition may be propelled without ejected propellant using a "bag on valve" system which utilizes air or nitrogen that is isolated from the remainder of the composition.

Wax

In certain embodiments, the composition includes a wax. By wax, it is meant one or more hydrophobic compounds that have a melting point (or melting range) that is in the range from 30° C. to 120° C., such as in the range from 45° C. to 100° C. In one embodiment, the wax component includes a wax compound having a melting point from about 75° C. to 100° C.

By "hydrophobic compound," it is meant a compound that includes a hydrophobic moiety that meets one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is not amphiphilic and, and such, does not include hydrophilic moieties, such as anionic, cationic, zwitterionic, or nonionic group, that is polar, including sulfate, sulfonate, carboxylate, phosphate, phosphonates, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the hydrophobic compound does not include hydroxyl moieties.

Suitable waxes include any of various hydrocarbons (straight or branched chain alkanes or alkenes, ketone, diketone, primary or secondary alcohols, aldehydes, sterol esters, alkanoic acids, turpenes, monoesters), such as those having a carbon chain length ranging from $C_{12}$-$C_{38}$. Also suitable are diesters or other branched esters. In one embodiment, the compound is an ester of an alcohol (glycerol or other than glycerol) and a $C_{18}$ or greater fatty acid.

Non-limiting examples include any of various natural waxes including lotus wax (e.g., Nelumbo Nucifera Floral Wax available from Deveraux Specialties, Silmar, Calif.); beeswax (e.g., White Beeswax SP-422P available from Strahl and Pitsch of West Babylon, N.Y.), insect waxes, sperm whale oil, lanolin, vegetable waxes such as canauba wax, jojoba oil, candelilla wax; mineral waxes such as paraffin wax; and synthetic waxes such as cetyl palmitate, lauryl palmitate, cetostearyl stearate, and polyethylene wax (e.g., PERFORMALENE 400, having a molecular weight of 450 and a melting point of 84° C., available from New Phase Technologies of Sugar Land, Tex.); and silicone waxes such as $C_{30-45}$ alkyl methicone and $C_{30-45}$ olefin (e.g., Dow Corning AMS-C30, having a melting point of 70° C., available from Dow Corning of Midland, Mich.). In certain embodiments, the wax component includes a high melting point ester of glycerol such as glycerol monostearate.

The amount of wax may be present in the composition from about 0.1% to about 5%, or from about 0.1% to about 2%, or from about 0.1% to about 1%.

Other Ingredients

Any of various other cosmetically-acceptable ingredients may be included in the composition in amounts so as to not counter the effects of the various other ingredients. For example, ingredients such as fragrances, dyes, preservatives, skin benefit agents, photostabilizers, anti-oxidants may be includes, in, for example total concentrations that are less than about 10%, such as less than about 5%, such as less than about 2%, e.g., less than about 1%. In certain embodiments, the composition is substantially free of ingredients that are insoluble in the volatile solvent.

Compositions of the present invention are generally provided in the form of a single phase solution of various ingredients in the volatile solvent with an optional propellant. The optional propellant generally exists as a vapor in equilibrium with liquid propellant that is dissolved in or is miscible with the remainder of the composition. In certain embodiments, the composition has at most 2% of insoluble solids or liquids dispersed therein.

EXAMPLES

The following non-limiting examples further illustrate the claimed invention:

Example I

Preparation of Inventive Examples

The following compositions, Inventive Examples Ex. 1-4, shown in Table 1, according to embodiments of the invention described herein were prepared:

TABLE 1

| | | Inventive Examples | | | |
|---|---|---|---|---|---|
| Trade Name | CTFA Name | Ex. 1 | Ex. 2 | Ex. 3 | Ex. 4 |
| SD Alcohol 40 B, 200 Proof (volatile solvent) | SD Alcohol 40 B, 200 Proof (Aapers) | 39.13 | 41.13 | 44.13 | 47.13 |
| Ascorbyl Palmitate | | 0.01 | 0.01 | 0.01 | 0.01 |
| Acrylates/Octylacrylamide Copolymer (film-forming polymer) | Dermacryl 79 (Akzo) | 2.50 | 2.50 | 2.50 | 2.50 |
| Homosalate (organic UV-filter) | Eusolex (Merck) | 15.00 | 15.00 | 10.00 | 8.00 |
| Oxybenzone (organic UV-filter) | Benzophenone - 3/Uvinul M40 (BASF) | 6.00 | 6.00 | 5.00 | 5.00 |
| Octisalate (organic UV-filter) | Octyl Salicylate | 5.00 | 5.00 | 5.00 | 4.00 |
| Avobenzone (organic UV-filter) | Neo Heliopan 357 (Symrise) | 3.00 | 3.00 | 3.00 | 3.00 |
| Octocrylene (organic UV-filter) | Neo heliopan 303 (Symrise) | 10.00 | 10.00 | 10.00 | 8.00 |
| Butyloctyl Salicylate | Halbrite BHB (C P Hall) | 5.00 | 0 | 0 | 0 |
| Diethylhexl 2,6 Naphtalate | CorapanTQ (C P Hall) | 0.10 | 0.10 | 0.10 | 0.10 |
| Lotus Wax (wax) | Deveraux | 0.10 | 0.10 | 0.10 | 0.10 |
| Dimethicone (and) Acrylates/Dimethicone Copolymer (film-forming polymer) | X-22-8247D (ShinEtsu) | 1.50 | 1.50 | 1.50 | 1.50 |
| Tocopheryl Acetate | Vit E Acetate | 0.25 | 0.25 | 0.25 | 0.25 |
| Retinyl Palmitate | Vit A Palmitate | 0.01 | 0.01 | 0.01 | 0.01 |
| Octyldodecyl Citrate Crosspolymer (and) Ethyl Methicone (and) Cetyl Dimethicone/ bis Vinyl Dimethicone Crosspolymer [1] | Blend | 12.00 | 15.00 | 18.00 | 20.00 |
| Fragrance | | 0.4 | 0.4 | 0.4 | 0.4 |
| TOTAL CONCENTRATE | | 68.0 | 68.0 | 68.0 | 68.0 |
| Dimethyl Ether (aerosol propellant) | | 32.0 | 32.0 | 32.0 | 32.0 |
| TOTAL | | 100.0 | 100.0 | 100.0 | 100.0 |

[1] A blend of 79.8% of octyldodecyl citrate polyester (COSMOSURF CE-100, a BFEPCA), 20% ethyl methicone (SILWAX D02, a water-insoluble, low-volatility, $C_2$-$C_8$, liquid silicone), and 0.2% of a copolymer of cetyl dimethicone and bis-vinyl dimethicone (SILWAX CR-5016, an alkyl-modified, silicone polymer), each available from SilTech.

Inventive Examples 1-4 were prepared by charging a vessel with the isopropanol (volatile solvent), adding acrylates/octylacrylamide copolymer and mixing until completely dissolved and then adding ascorbyl palmitate and mixing until homogeneous. In a secondary container an oil/sunscreen phase was prepared by blending homosalate, oxybenzone, octisalate, avobenzone, octocrylene, diethylhexyl 2,6 naphtalate, butyloctyl salicylate (only in the case of Ex. 1), lotus wax, dimethicone and acrylates/dimethicone copolymer and heating the mixture up to 75-80° C., until the sunscreen powders were completely dissolved and homogeneous. This phase was then cooled to 30° C. The oil/sunscreen phase was slowly added to the alcohol phase. The remainder of the ingredients, including tocopheryl acetate, retinyl palmitate, as well as a pre-blend of octyldodecyl citrate crosspolymer, ethyl methicone and cetyl dimethicone/bis vinyl dimethicone crosspolymer; and fragrance were then added.

Example II

Evaluation of Inventive Examples and Comparative Examples

Comparative Examples, Comp. 1-6 were prepared (as concentrates only—no propellant) in a manner otherwise similar to Inventive Example Ex. 1, except that (1) the copolymer of cetyl dimethicone/bis-vinyl dimethicone was omitted in certain cases; (2) the relative proportions of octyldodecyl citrate polyester were adjusted in some cases; and (3) ethyl methicone was replaced with lauryl ($C_{12}$) or cetyl ($C_{18}$) dimethicone, respectively.

The concentrate of Inventive Example Ex. 1, as well as Comparative Examples Comp. 1, were each separately pump sprayed onto the wet arm of a human subject. Inventive Example Ex. 1 (79.8:20:0.2 ratio of COSMOSURF CE-100 to SILWAX D-02, with SILWAX CR-5016) did not exhibit whitening upon application to the wet skin, dried well and formed an invisible film on the skin. Comparative Example, Comp. 1 (no SILWAX D-02 and no SILWAX CR-5016) exhibited temporary whitening immediately upon application to the wet skin, did not exhibit good aesthetics, e.g. it had a heavy feel on skin, and tended to peel on contact with wet skin. Comparative Example, Comp. 2 (90:10 ratio of COSMOSURF CE-100 to SILWAX D-02, and no SILWAX CR-5016) showed less whitening than Comp. 1, but still exhibited an unacceptable amount of temporary whitening immediately upon application to the wet skin. Inventive Example, Ex. 5 (80:20 ratio of COSMOSURF CE-100 to SILWAX D-02, and no SILWAX CR-5016) showed very slight, but acceptable, temporary whitening immediately upon application to the wet skin.

Example III

Evaluation of Additional Comparative Examples

Comparative Examples, Comp. 4-6 were prepared (again, as concentrates) in a manner otherwise similar to Example Ex. 1, except that ethyl methicone was replaced with a methicone having an alkyl substitution with a greater length carbon chain.

Specifically, Comparative Example, Comp. 4 was identical to Inventive Example, Ex. 1, except that ethyl methicone was replaced with cetyl dimethicone (4:1 ratio of COSMOSURF CE-100 to cetyl dimethicone, and no SILWAX CR-5016). It showed both unacceptable haziness and slight but unacceptable temporary whitening immediately upon application to the wet skin.

Furthermore, Comparative Example, Comp. 5 was identical to Comparative Example, Comp. 4, except that the ratio of COSMOSURF CE-100 to cetyl dimethicone was 1:1. It showed unacceptable peeling on skin.

Furthermore, Comparative Example, Comp. 6 was identical to Comparative Example, Comp. 4, except that cetyl dimethicone was replaced with lauryl dimethicone. It showed temporary unacceptable haziness immediately upon application to the wet skin.

The results in Examples II and III suggest that if the octyldodecyl citrate polyester and ethyl methicone are present in a weight ratio that is from about 3:1 to 4.25:1, the composition provides an aesthetic, non-whitening film that resists water on the skin and allows a transparent film to form thereon. If these ingredients are in a ratio above that range, the composition exhibits too much temporary whitening immediately upon application to the wet skin. If these ingredients are in a ratio below that range, or if the ethyl methicone is replaced with, for example, a $C_{12}$ or $C_{18}$ alkyl methicone, the resulting composition exhibits peeling on the skin and/or temporary haziness upon application to the wet skin.

Example IV

Evaluation of Sun Protection Factor (SPF) of Inventive Examples

Four inventive example compositions, Inventive Examples, Ex. 1-4 were tested for sun protection factor (SPF) using a conventional in-vivo static SPF test method that included an 80 minute water immersion following application to dry skin. The compositions had an SPF reported as 89.62, 75.22, 54.85, and 36.22 respectively.

The same compositions were tested using a modified method, identical to the conventional method, except the compositions were applied to wet skin. Specifically, the test subjects immersed themselves in a spa for 5 minutes, exited the spa, remained at ambient temperature, and within 5 minutes from exiting the spa, the test materials was applied to the wet skin of the subject. The compositions had a SPF value of 87.29, 73.82, 54.33, and 35.2 respectively. These results show, surprisingly, that the inventive compositions lost only a small fraction (less than 3%) of their SPF when applied to wet skin as compared with when applied to dry skin, according to the conventional in-vivo method.

The invention claimed is:

1. A composition comprising:
   a volatile solvent;
   an organic UV-filter dissolved in the volatile solvent;
   a water-insoluble, low-volatility, $C_2$-$C_8$, liquid silicone selected from the group consisting of ethyl methicone and caprylyl methicone dissolved in the volatile solvent;
   a branched fatty acid ester of a polyprotic carboxylic acid dissolved in the volatile solvent; and
   a film-forming polymer, wherein the branched fatty acid ester of a polyprotic carboxylic acid and the water-insoluble, low-volatility, $C_2$-$C_8$, liquid silicone are present in a ratio from about 3:1 to 4.25:1, wherein the composition is substantially free of water.

2. The composition of claim 1, wherein the branched fatty acid ester of a polyprotic carboxylic acid is an octyldodecyl citrate polyester.

3. The composition of claim 1, wherein the branched fatty acid ester of a polyprotic carboxylic acid and the water-insoluble, low-volatility, $C_2$-$C_8$, liquid silicone are present in a ratio from 3.5:1 to 4:1.

4. The composition of claim 1, wherein the organic UV-filter is selected from the group consisting of octocrylene, a benzotriazole, anisotriazine, an ester of salicylic acid, an ester of cinnamic acid and a derivative of a benzoylmethane.

5. The composition of claim 1, further comprising an aerosol propellant.

6. The composition of claim 5, wherein the aerosol propellant is dimethyl ether.

7. The composition of claim 1, further comprising a wax.

8. The composition of claim 1, further comprising from 0.1 to about 5 percent of lotus wax.

9. The composition of claim 1 comprising from about 10% to about 60% by weight of said volatile solvent.

10. The composition of claim 9 comprising less than 0.1 percent of water.

11. The composition of claim 4 comprising less than 0.1 percent of water and from about 10 percent to about 60 percent of said volatile solvent, wherein said volatile solvent is selected from the group consisting of ethanol, propanol and isopropanol.

12. A composition comprising:
from 10 percent to 60 percent of a volatile solvent selected from the group consisting of ethanol, propanol and isopropanol;
an organic UV-filter dissolved in the volatile solvent;
a water-insoluble, low-volatility, $C_2$-$C_8$, liquid silicone selected from the group consisting of ethyl methicone and caprylyl methicone dissolved in the volatile solvent;
a branched fatty acid ester of a polyprotic carboxylic acid dissolved in the volatile solvent; and
a film-forming polymer, wherein the branched fatty acid ester of a polyprotic carboxylic acid and the water-insoluble, low-volatility, $C_2$-$C_8$, liquid silicone are present in a ratio from about 3:1 to 4.25:1,
wherein the composition comprises less than one percent of water.

13. The composition of claim 12 further comprising an aerosol propellant.

14. The composition of claim 12, further comprising a wax.

15. The composition of claim 13, wherein the aerosol propellant is dimethyl ether.

16. The composition of claim 1, further comprising from 0.1 to about 5 percent of lotus wax.

17. The composition of claim 12, wherein the organic UV-filter is selected from the group consisting of octocrylene, a benzotriazole, anisotriazine, an ester of salicylic acid, an ester of cinnamic acid and a derivative of a benzoylmethane.

* * * * *